United States Patent [19]

Tice

[11] Patent Number: 5,298,481

[45] Date of Patent: Mar. 29, 1994

[54] 6-ARYLPYRIMIDINES AND HERBICIDAL USE

[75] Inventor: Colin M. Tice, Melrose Park, Pa.

[73] Assignee: Rohm and Haas Company, Philadelphia, Pa.

[21] Appl. No.: 916,315

[22] Filed: Jul. 17, 1992

[51] Int. Cl.$^5$ .................. C07D 239/32; C07D 239/46; C07D 401/04; A01N 43/54

[52] U.S. Cl. ........................ 504/242; 504/243; 544/309; 544/310; 544/311; 544/312; 544/314; 544/319; 544/320; 544/321; 544/330; 544/331; 544/332

[58] Field of Search ............... 71/92; 544/309, 310, 544/311, 312, 314, 319, 320, 321, 330, 331, 332; 504/242, 243

[56] References Cited

U.S. PATENT DOCUMENTS 3,214,430 10/1965 Rorig et al. ............... 260/256.4

FOREIGN PATENT DOCUMENTS 168262 1/1986 European Pat. Off. .
1003802 9/1965 United Kingdom .

OTHER PUBLICATIONS

Takaya et al., Chemical Abstracts, vol. 105, entry 78951s (1986).

Primary Examiner—John M. Ford
Attorney, Agent, or Firm—Terence P. Strobaugh; Clark R. Carpenter

[57] ABSTRACT

A class of 6-arylpyrimidines which is useful in the control of weeds is of the general formulae:

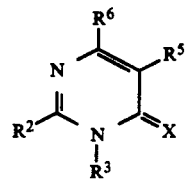

I and

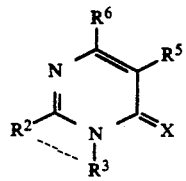

II wherein $R^2$ is selected from hydrogen, halo, substituted or unsubstituted alkyl, haloalkyl, polyhaloalkyl, haloalkenyl, polyhaloalkenyl, haloalkynyl, polyhaloalkynyl, alkenyl, alkynyl, alkoxy, alkylthio, alkoxycarbonylalkyl, cyano, alkoxyalkyl, alkoxycarbonyl, cycloalkyl, aralkyl, alkylamino, dialkylamino, or dialkylaminocarbonyl group; $R^3$ is an alkyl, alkenyl, alkynyl, or haloalkyl group; $R^5$ is an alkyl, alkenyl, alkynyl, alkenynyl, or alkoxyalkyl, group; $R^6$ is an aryl group (e.g. aromatic ring); and X is oxygen or sulfur. $R^2$ and $R^3$ may form a fused ring.

9 Claims, No Drawings

6-ARYLPYRIMIDINES AND HERBICIDAL USE

BACKGROUND OF THE INVENTION

A need continues for novel and improved herbicidal compounds and compositions. This is particularly so since the targets of herbicides can become resistant to known herbicides over time. Additionally, economic and environmental considerations can favor herbicides having different modes of performance than those currently used. This invention relates to novel arylpyrimidines and their use as broad spectrum herbicides.

SUMMARY OF THE INVENTION

6-Arylpyrimidines which are useful in the control of weeds have been discovered. These compounds are of the general formula:

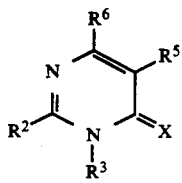

wherein $R^2$ is a hydrogen, halo, substituted or unsubstituted alkyl, haloalkyl, alkenyl, alkynyl, alkoxy, alkylthio, alkoxycarbonylalkyl, cyano, alkoxyalkyl, polyhaloalkyl, haloalkenyl, polyhaloalkenyl, haloalkynyl, polyhaloalkynyl, alkoxycarbonyl, cycloalkyl, aralkyl, alkylamino, dialkylamino, or dialkylaminocarbonyl group; $R^3$ is alkyl, alkenyl, alkynyl or haloalkyl; $R^5$ is an alkyl, alkenyl, alkynyl, alkenynyl or alkoxyalkyl group; $R^6$ is an aryl or heteroaromatic group; and X is oxygen or sulfur. Additional embodiments include those compounds in which the $R^2$ and $R^3$ substituents are fused into a ring moiety. Also included are methods of preparing these new compounds as well as methods of using the compounds as herbicides

EMBODIMENTS OF THE INVENTION

Compounds

An embodiment of the present invention are compounds of the general formula:

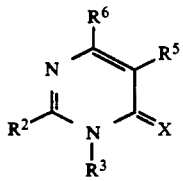

I wherein $R^2$ is hydrogen, halo, substituted or unsubstituted alkyl, haloalkyl, alkenyl, alkynyl, alkoxy, alkylthio, alkoxycarbonylalkyl, cyano, alkoxyalkyl, polyhaloalkyl, haloalkenyl, polyhaloalkenyl, haloalkynyl, polyhaloalkynyl, alkoxycarbonyl, cycloalkyl, aralkyl, alkylamino, dialkylamino, or dialkylaminocarbonyl group; $R^3$ is alkyl, alkenyl, alkynyl or haloalkyl group; $R^5$ is an alkyl, alkenyl, alkynyl, alkenynyl, or alkoxyalkyl group; $R^6$ is an aryl or heteroaromatic group which may be substituted or unsubstituted; and X is oxygen or sulfur. In some embodiments $R^2$ and $R^3$ are fused into a ring moiety.

$R^2$ is a hydrogen, halo, alkyl, alkenyl, alkynyl, alkoxy, alkylthio, alkoxyalkyl, alkoxycarbonyl, alkoxycarbonylalkyl, haloalkyl, polyhaloalkyl, cycloalkyl, haloalkenyl, polyhaloalkenyl, haloalkynyl, polyhaloalkynyl, aralkyl, alkylamino, dialkylamino, dialkylaminocarbonyl, or cyano group. Preferred $R^2$ groups are hydrogen, straight ($C_1$–$C_6$)alkyl, branched ($C_3$–$C_8$)alkyl, ($C_2$–$C_6$)alkenyl, ($C_2$–$C_6$)alkynyl, halo($C_1$–$C_6$)alkyl or polyhalo($C_1$–$C_6$)alkyl, halo($C_2$–$C_6$)alkenyl or polyhalo($C_2$–$C_6$)alkenyl, halo($C_2$–$C_6$)alkynyl or polyhalo($C_2$–$C_6$)alkynyl, ($C_1$–$C_4$)alkoxy($C_1$–$C_4$)alkyl, ($C_1$–$C_6$)alkylthio, ($C_1$–$C_6$)alkoxy, ($C_1$–$C_3$)alkoxycarbonyl, ($C_1$–$C_3$)alkoxycarbonyl($C_1$–$C_3$)alkyl, ar($C_1$–$C_4$)alkyl, cyclo)$C_3$–$C_7$)alkyl, ($C_1$–$C_3$)alkylamino, di($C_1$–$C_3$)alkylamino, di($C_1$–$C_3$)alkylaminocarbonyl, halo and cyano. Preferred straight ($C_1$–$C_6$)alkyls and branched ($C_3$–$C_8$)alkyls are methyl, ethyl, n-propyl, n-butyl, n-hexyl, i-propyl, i-butyl and t-butyl; more preferably methyl, ethyl, n-propyl, i-propyl and t-butyl. A preferred ($C_2$–$C_6$)alkenyl is allyl. Preferred ($C_1$–$C_6$)alkoxys are ($C_1$–$C_5$)alkoxys, more preferably methoxy and ethoxy. A preferred ($C_1$–$C_3$)alkoxycarbonyl is ethoxycarbonyl. Preferred ($C_2$–$C_6$)alkynyls are but-2-ynyl, but-3-ynyl, and prop-2-ynyl. Preferred halos are fluoro, bromo, and chloro; more preferably chloro and bromo. Preferred halo($C_1$–$C_6$)alkyls and polyhalo($C_1$–$C_6$)alkyls are halo($C_1$–$C_3$)alkyls and polyhalo($C_1$–$C_3$)alkyls, more preferably trifluoromethyl or pentafluoroethyl. Preferred ($C_1$–$C_6$)alkylthios are ($C_1$–$C_5$)alkylthios, more preferably methylthio. A preferred ($C_1$–$C_4$)alkoxy($C_1$–$C_4$)alkyl is methoxymethyl. A preferred ar($C_1$–$C_4$)alkyl is benzyl. Preferred cyclo($C_3$–$C_7$)alkyls are cyclopropyl and cyclobutyl. A preferred di($C_1$–$C_3$)alkylamino is dimethylamino. A preferred di($C_1$–$C_3$)alkylaminocarbonyl is dimethylaminocarbonyl.

$R^3$ is an alkyl, alkenyl, alkynyl or haloalkyl group. Preferred $R^3$ substituents are ($C_1$–$C_4$)alkyl, ($C_3$–$C_6$)alkenyl, ($C_3$–$C_6$)alkynyl, halo- or polyhalo($C_1$–$C_6$)alkyl groups. Preferred ($C_1$–$C_4$)alkyls are methyl and ethyl. Preferred ($C_3$–$C_6$)alkynyls are ($C_3$–$C_4$)alkynyls, more preferably prop-2-ynyl. Preferred ($C_3$–$C_6$)alkenyls are ($C_3$–$C_4$)alkenyl, more preferably allyl. Preferred halo- or polyhalo($C_1$–$C_6$)alkyls are halo- or polyhalo($C_1$–$C_4$)alkyls, more preferably trifluoromethyl.

$R^5$ is an alkyl, alkenyl, alkynyl, alkenynyl, or alkoxyalkyl group. Preferably, $R^5$ is a ($C_1$–$C_4$)alkyl; ($C_2$–$C_6$)alkenyl; ($C_2$–$C_6$)alkynyl or ($C_5$–$C_6$)alkenynyl group, each of which may be optionally substituted with up to five halogens; or a ($C_1$–$C_4$)alkoxy($C_1$–$C_4$)alkyl group. Preferred ($C_1$–$C_4$)alkyl groups are methyl and ethyl. Preferred ($C_2$–$C_6$)alkenyl groups are ($C_3$–$C_4$)alkenyls, such as allyl. More preferred ($C_2$–$C_6$)alkynyl groups are ($C_3$–$C_4$)alkynyl, such as propynyl and butynyl, more preferably prop-2-ynyl. Preferred ($C_1$–$C_4$)alkoxy($C_1$–$C_4$)alkyls are ($C_1$–$C_2$)alkoxy($C_1$–$C_2$)alkyls, more preferably methoxymethyl or 2-methoxyethyl. A preferred ($C_5$–$C_6$)alkenynyl is pent-4-en-2-ynyl.

$R^6$ is an aryl or heteroaromatic group, preferably furyl, phenyl, pyridyl, or thienyl, and may be substituted with up to three substituents independently selected from bromo; chloro; fluoro; ($C_1$–$C_{12}$)alkyl, preferably ($C_1$–$C_6$)alkyl; cyclo($C_3$–$C_8$)alkyl, preferably cyclo($C_5$–$C_6$)alkyl; ($C_2$–$C_{12}$)alkenyl, preferably ($C_2$–$C_6$)alkenyl; cyclo($C_3$–$C_8$)alkenyl; ($C_2$–$C_{12}$)alkynyl, preferably ($C_2$–$C_6$)alkynyl; halo($C_1$–$C_{12}$)alkyl, preferably halo($C_1$–$C_6$)alkyl; polyhalo($C_1$–$C_{12}$)alkyl, preferably polyhalo($C_1$–$C_6$)alkyl; halo($C_2$–$C_{12}$)alkenyl, preferably halo($C_2$-$C_6$)alkenyl; polyhalo($C_2$-$C_{12}$)alkenyl, preferably polyhalo($C_2$-$C_6$)alkenyl; halo($C_2$-$C_6$)alkynyl; polyhalo($C_2$-$C_6$)alkynyl; ($C_1$-$C_{12}$)alkoxy, preferably ($C_1$-$C_6$)alkoxy; ($C_1$-$C_{12}$)alkylthio, preferably ($C_1$-$C_6$)alkylthio; ($C_1$-$C_{12}$)alkylsulfonyl; ($C_1$-$C_{12}$)alkylsulfinyl; phenyl; phen($C_1$-$C_{12}$)alkyl; phen($C_2$-$C_{12}$)alkenyl; phen($C_2$-$C_{12}$)alkynyl; cyano; halo($C_1$-$C_6$)alkoxy, carbo($C_1$-$C_6$)alkoxy, and nitro. Substituent groups can be branched or unbranched. A preferred aryl group is unsubstituted phenyl.

In some embodiments $R^2$ and $R^3$ are fused into a ring moiety (i.e., described sometimes herein as "$R^2$-$R^3$ link"). Such $R^2$-$R^3$ links are preferably a two to five membered link, more preferably a three or four membered link. Such links are composed of all carbons atoms or are composed of one or more carbon, oxygen and sulfur atoms in differing ratios. Non-limiting examples include —($CH_2$)$_{2-5}$— and —$SCH_2CH_2$—. Other links could include both oxygen and sulfur atoms as well as carbon atoms. The structure of such a linked compound may be illustrated as follows:

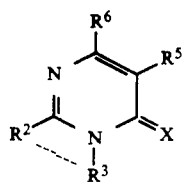

II

In the embodied compounds, X is oxygen or sulfur, preferably oxygen.

Compounds encompassed by the present invention include, but are not limited to, those illustrated in Tables 1 and 2. The synthesis methods were the steps of Synthesis Procedure A(1) followed by the steps of Synthesis Procedure A(2) described hereinafter.

TABLE 1

III

| Compound | $R^2$ | $R^3$ | $R^5$ | $R^6$ | MP °C. |
|---|---|---|---|---|---|
| 1 | —$CH_3$ | —$CH_3$ | —$CH_2C\equiv CH$ | -Phenyl | 142–144 |
| 2 | —$CH_3$ | —$CH_2C\equiv CH$ | —$CH_2C\equiv CH$ | -Phenyl | 155–156 |
| 3 | —$CH_2CH_2CH_3$ | —$CH_3$ | —$CH_2C\equiv CH$ | -Phenyl | 102–103 |
| 4 | —H | —$CH_3$ | —$CH_2C\equiv CH$ | -Phenyl | 194–196 |

The following Table 2 compounds were synthesized using Synthesis Procedure B and have a fused link with bonding at the $R^2$ and $R^3$ positions, as in drawing II above. For instance, Compound 5 has the following drawing (IV):

TABLE 2

IV

| Compound | $R^2$-$R^3$ Link | $R^5$ | $R^6$ | MP |
|---|---|---|---|---|
| 5 | —$CH_2CH_2CH_2CH_2$— | —$CH_2C\equiv CH$ | -Phenyl | >105(dec) |
| 6 | —$SCH_2CH_2$—* | —$CH_2C\equiv CH$ | -Phenyl | 179–183 |
| 7 | —$CH_2CH_2CH_2CH_2$— | —$CH_3$ | -Phenyl | oil** |

*the sulfur atom (S) of the —$SCH_2CH_2$— link is bonded to the carbon atom at the 2 position of the pyrimidinone ring and the carbon atom at the end of the link is bonded to the nitrogen atom (N) at the 3 position of the ring.
**NMR data for compound 7 is $^1$H-NMR(CDCl$_3$)δ2.0(4H, m), 2.15(3H, s), 3.0(2H, t), 4.05(2H, t), 7.4–7.6(5H).

Methods of Preparation

The 6-arylpyrimidines of the present invention may be prepared by synthetic routes such as that illustrated below.

Synthesis Procedure A(1)—Precursor Material

An amidine hydrochloride or other salt is heated with a beta-keto ester in a solvent in the presence of a base to neutralize the hydrochloric acid. Solvents usable include xylene or toluene. Sodium acetate can be the base:

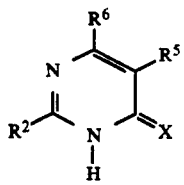

V

Method A(1)—Specific Example—Preparation of 2-methyl-6-phenyl-5-propargyl-4(3H)-pyrimidinone To a stirred suspension of 8.00 g (84.6 mmol) of acetamidine hydrochloride in 100 mL of methanol was added 4.56 g (84.4 mmol) of solid sodium methoxide. The mixture was stirred for 40 min at room temperature and rotovaped to remove the methanol. The residue was suspended in 75 mL of ethanol and a solution of 6.19 g (26.9 mmol) of ethyl 2-benzoyl-pent-4-ynoate in 75 mL of toluene was added. The mixture was heated to reflux with a Dean Stark trap and the first 80 mL of distillate was collected and discarded. An 80 mL portion of toluene was added and the mixture was heated at reflux for two weeks. The mixture was allowed to cool, diluted with 70 mL of ether and extracted with two 50 mL portions of 5% aqueous sodium hydroxide. The aqueous extracts were acidified to pH 1 and washed with two 75 mL portions of ethyl acetate. The pH of the aqueous phase was adjusted to 10 and the white precipitate that formed was collected by filtration. Drying furnished 1.76 g (29%) of 2-methyl-6-phenyl-5-propargyl-4(3H)-pyrimidinone, mp 220°-225° C., $^1$H-NMR (d6-DMSO) δ 2.3 (3H,s), 2.68(1H,t,J=4), 3.20(2H,d,J=4), 7.45(3H,m), 7.65(2H,m).

Synthesis Procedure A(2)—General Description

A precursor compound having the structure of formula I above with hydrogen (H) in the $R^3$ substituent position is selected. Reaction with $R^3Y$ is performed in a base-solvent mixture. Y can be a halogen, alkanesulfonate, haloalkanesulfonate or optionally substituted benzenesulfonate. The bases can be sodium hydride, alkali metal hydroxides, alkali metal carbonates or alkali metal alkoxides. The solvent can be alcohol, ketone, water, ether, dimethyl sulfoxide or dimethyl formamide. A mixture of N- and O- alkylated products results.

Method A(2)—Specific Example—Preparation of 2,3-dimethyl-6-phenyl-5-propargyl-4(3H)-pyrimidinone (Compound 1)

A mixture of 0.76 g (3.4 mmol) of 2-methyl-6-phenyl-5-propargyl-4(3H)-pyrimidinone, 0.72 g (5.2 mmol) of anhydrous potassium carbonate, 0.32 mL (5.1 mmol) of methyl iodide and 20 mL of methyl ethyl ketone was heated at reflux for 6 h. The mixture was cooled, diluted with 40 mL of water and extracted with two 60 mL portions of ethyl acetate. The ethyl acetate extracts were dried and rotovaped to leave 0.75 g of crude product. This material was purified by flash chromatography on silica gel to afford 0.71 g of 2,3-dimethyl-6-phenyl-5-propargyl-4(3H)-pyrimidinone as a white solid, mp 142°-144° C., $^1$H-NMR (CDCl$_3$) δ 2.10(3H,t,J=4), 2.60(3H,s), 3.40(2H,d,J=4), 3.60(3H,s), 7.45(3H,m), 7.65(2H,m); IR(nujol) 3200, 1650 cm$^{-1}$.

Calculated for C$_{15}$H$_{14}$N$_2$O: C 75.61, H 5.92, N 11.76. Found: C 75.33, H 5.72, N 11.63.

Method B—General Description

Direct condensation of an N-alkylamidine and a beta-keto ester is performed by warming the reagents neat or in a solvent such as tetrahydrofuran or methanol:

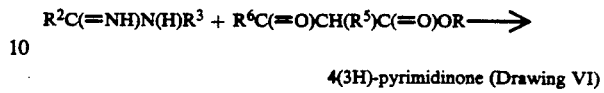

4(3H)-pyrimidinone (Drawing VI)

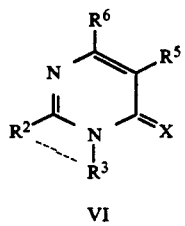

VI

Method B—Specific Example—Preparation Of 6-Phenyl-5-propargyl-2,3-tetrahydrobenzo-4(3H)-pyrimidinone (Compound 5)

A suspension of 5.00 g (37.1 mmol) of 2-iminopiperidine hydrochloride and 2.00 g (37.1 mmol) of sodium methoxide in methanol was stirred at room temperature for 0.5 h and then rotovaped to dryness. A solution of 4.23 g (18.4 mmol) of ethyl 2-benzoylpent-4-ynoate in 10 mL of ethanol was added. The mixture was stirred at room temperature for 3 weeks, diluted with 100 mL of 5% aqueous hydrochloric acid and washed with two 100 mL portions of ether. The aqueous phase was basified by cautious addition of solid sodium carbonate and extracted with two 100 mL portions of ether. These ether extracts were combined, dried and concentrated to leave 1.88 g of a viscous yellow oil. This material was purified by flash chromatography on a column of 30 g of silica gel to furnish 1.49 g (30%) of 6-phenyl-5-propargyl-2,3-tetrahydrobenzo-4(3H)-pyrimidinone (Compound 5) as a solid, mp>105° C. (dec). $^1$H-NMR (CDCl$_3$) δ 1.9(4H,m), 2.1(1H,t), 2.9(2H,t), 3.35(2H,d), 4.0(2H,t), 7.4(3H,m), 7.65(2H,m).

Methods of Use

In another aspect, this invention relates to a method of controlling weeds comprising applying to said weed or the locus of said weed or to the surface of the growth medium of said weed a herbicidally effective amount of a compound of the formula:

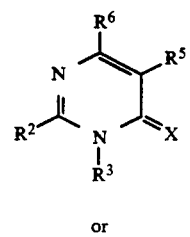

I or

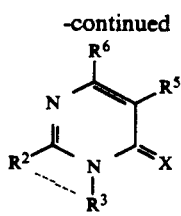

wherein R² is a hydrogen, halo, substituted or unsubstituted alkyl, alkenyl, alkynyl, alkoxy, alkylthio, alkoxycarbonylalkyl, haloalkyl, polyhaloalkyl, haloalkenyl, polyhaloalkenyl, haloalkynyl, polyhaloalkynyl, cyano, alkoxyalkyl, alkoxycarbonyl, cycloalkyl, aralkyl, alkylamino, dialkylamino, or dialkylaminocarbonyl group; R³ is an alkyl, alkenyl, alkynyl, or haloalkyl group; R⁵ is an alkyl, alkenyl, alkynyl, alkenynyl or alkoxyalkyl group; R⁶ is an aryl group (e.g. aromatic ring) which can be substituted or unsubstituted; and X is oxygen or sulfur. R² and R³ may be linked to form a ring.

The particulars as to the substituents and preferences therefore are as stated herein above in the Compound Embodiments.

The compounds of the invention are useful as preemergence and postemergence herbicides. In general, they require lower doses to control weeds preemergence. Preemergence herbicides are usually applied to the soil either before, during or after seeding, but before the crop emerges. Post emergence herbicides are applied after the plants have emerged and during their growth period. The embodied compounds generally show selectivity to several agronomically important crops, such as corn, cotton, rice, soybean, sugarbeet, sunflower and wheat.

Under some conditions the compounds of the invention may be incorporated into the soil or other growth medium prior to planting a crop. This incorporation may be by any convenient means, including mixing with the soil, applying the compound to the surface of the soil and then dishing or dragging into the soil to the desired depth, or by employing a liquid carrier.

The 6-arylpyrimidines of the present invention can be applied to various loci such the soil or the foliage. For such purposes these compounds can be used in the technical or pure form as prepared, as solutions or as formulations. The compounds are usually taken up in a carrier or are formulated so as to render them suitable for subsequent dissemination as herbicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Co., Ridgewood, N.J.

The 6-arylpyrimidines can be applied as herbicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and weeds to be controlled, but the preferred effective amount is usually from about 0.01 lb. to about 10 lbs. per acre of the active ingredient.

As a soil treatment the chemical can be incorporated in the soil or applied to the surface usually at a rate of from about 0.01 to about 10 lbs. per acre. As a foliar spray, the toxicant is usually applied to growing plants at a rate of from about 0.01 to about 10 lbs. per acre.

The 6-arylpyrimidines of the invention can also be mixed with fertilizers or fertilizing materials before their application. In one type of solid fertilizing composition in which the arylpyrimidines can be used, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The 6-arylpyrimidine will commonly be from about 5% to about 25% of the fertilizing composition. These compositions provide fertilizing materials which promote the rapid growth of desired plants, and at the same time control the growth of undesired plants.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

CARBOXYLIC ACIDS AND DERIVATIVES 2,3,6-Trichlorobenzoic acid and its salts; 2,3,5,6-tetrachlorobenzoic acid and its salts; 2-methoxy-3,5,6-trichlorobenzoic acid and its salts; 2-methoxy-3,6-dichlorobenzoic acid and its salts; 2-methyl-3,6-dichlorobenzoic acid and its salts; 2,3-dichloro-6-methylbenzoic acid and its salts; 2,4-dichlorophenoxyacetic acid and its salts and esters; 2,4,5-trichlorophenoxyacetic acid and its salts and esters; 2-methyl-4-chlorophenoxyacetic acid and its salts and esters; 2-(2,4,5-trichlorophenoxy)propionic acid and its salts and esters; 4-(2,4-dichlorophenoxy)butyric acid and its salts and esters; 4-(2-methyl-4-chlorophenoxy)butyric acid and its salts and esters; 2,3,6-trichlorophenylacetic acid and its salts; 3,6-endoxohexahydrophthalic acid and its salts; dimethyl 2,3,5,6-tetrachloroterephthalate; trichloroacetic acid and its salts; 2,2-dichloropropionic acid and its salts; 2,3-dichloroisobutyric acid and its salts; isopropylammonium 2-(4-isopropyl-4-methyl-5-oxo-2-yl)nicotinate; 2-[4,5-dihydro-4-methyl-4-(1-methylethyl)-5-oxo-1H-imidazol-2-yl]-3-quinolinecarboxylic acid; 6-(4-isopropyl-4-methyl-5-oxo-2-imidazolin-2-yl)-m-toluic acid methyl ester and 6-(4-isopropyl-4-methyl-5-oxo-2-imidazolin-2-yl)-p-toluic acid methyl ester; N-(phosphomethyl)glycine isopropylammonium salt; [3,5,6-trichloro-(2-pyridinyl)oxy]acetic acid; 3,7-dichloro-8-quinolinecarboxylic acid; ammonium DL-homoalanin-4-yl(methyl)phosphinate.

CARBAMIC ACID DERIVATIVES

Ethyl N,N-di(n-propyl)thiolcarbamate; n-propyl N,N-di(n-propyl)thiolcarbamate; ethyl N-ethyl-N-(n-butyl)thiolcarbamate; n-propyl-N-ethyl-N-(n-butyl)thiolcarbamate; 2-chloroallyl N,N-diethyldithiocarbamate; isopropyl N-phenylcarbamate; isopropyl N-(m-chlorophenyl)carbamate; 4-chloro-2-butynyl-N-(m-chlorophenyl)carbamate; methyl N-(3,4-dichlorophenyl)carbamate; dinitro-o-(sec-butyl)phenol and its salts; pentachlorophenol and its salt; S-(4-chlorobenzyl)-N,N-diethylthiolcarbamate;

SUBSTITUTED UREAS

2-Chloro-N-[(4-methoxy-6-methyl-1,3,5-triazin-2-yl)aminocarbonyl]benzenesulfonamide; 3-(3,4-dichlorophenyl)-1,1-dimethylurea; 3-phenyl-1,1-dimethylurea; 3-(3,4-dichlorophenyl)-3-methoxy-1,1-dimethylurea; 3-(4-chlorophenyl)-3-methoxy-1,1-dimethylurea; 3-(3,4-dichlorophenyl)-1-n-butyl-1-methylurea; 3-(3,4-dichlorophenyl)-1-methoxy-1-methylurea; 3-(4-chlorophenyl)-1-methoxy-1-methylurea; 3-(3,4-dichlorophenyl)-1,1,3-trimethylurea; 3-(3,4-dichlorophenyl)diethylurea; dichloral urea; methyl 2-[[[[(4,6-dimethyl-2-pyrimidinyl)amino]-carbonyl]amino]sulfonyl]benzoate; N-((6-methoxy-4-methyl-1,3,5-triazin-2-yl)aminocarbonyl)-2-(2-chloroethoxy)benzene sulfonamide; 2-[[[(4-chloro-6-methoxypyrimidine-2-yl)aminocarbonyl]amino]sulfonyl]benzoic acid, ethyl ester; methyl 2-[[[[(4-methoxy-6-methyl-1,3,5-triazin-2-yl)amino]carbonyl]amino]sulfonyl]benzoate; methyl 3-[[(4-methoxy-6-methyl-1,3,5-triazin-2-yl)aminocarbonyl]-aminosulfonyl]-2-thiophene-carboxylate; methyl 2-[[[[[(4,6-dimethoxypyrimidin-2-yl)amino]carbonyl]-amino]sulfonyl]-methyl]benzoate; methyl 2-[[[[(4-methoxy-6-methyl-1,3,5-triazin-2-yl)methylamino]carbonyl]amino]sulfonyl]benzoate;

SUBSTITUTED TRIAZINES

2-Chloro-4,6-bis(ethylamino)-s-triazine; 2-chloro-4-ethylamino-6-isopropylamino-s-triazine; 2-chloro-4,6-bis(3-methoxy-n-propylamino)-s-triazine; 2-methoxy-4,6-bis(isopropylamino)-s-triazine; 2-chloro-4-ethylamino-6-(3-methoxy-n-propylamino)-s-triazine; 2-methylmercapto-4,6-bis(isopropylamino)-s-triazine; 2-methylmercapto-4,6-bis(ethylamino)-2-triazine; 2-methylmercapto-4-ethylamino-6-isopropylamino-s-triazine; 2-chloro-4,6-bis(isopropylamino)-s-triazine; 2methoxy-4-ethylamino-6-isopropylamino-s-triazine; 2-methylmercapto-4-(2-methoxyethylamino)-6-isopropylamino-s-triazine; 4-amino-6-(t-butyl)-3-(methylthio)-1,2,4-triazine-5(4H)-one;

DIPHENYL ETHER DERIVATIVES 2,4-Dichloro-4'-nitrodiphenyl ether; 2,4,6-trichloro-4'-nitrodiphenyl ether; 2,4-dichloro-6-fluoro-4'-nitrodiphenyl ether; 3methyl-4'-nitrodiphenyl ether; 3,5-dimethyl-5'-nitrodiphenyl ether; 2,4'-dinitro-4-(trifluoromethyl)diphenyl ether; 2,4-dichloro-3'-methoxy-4'-nitrodiphenyl ether; sodium 5-(2-chloro-4-(trifluoromethyl)phenoxy)-2-nitrobenzoate; 2-chloro-1-(3-ethoxy-4-nitrophenoxy)-4-(trifluoromethyl)benzene; 1-(carboethoxy)ethyl 5-[2-chloro-4-(trifluoromethyl)-phenoxy]-2-nitrobenzoate; 5-[2-chloro-4-(trifluoromethyl)phenoxy]-N-(methylsulphonyl)-2-nitrobenzamide;

ANILIDES

2-Chloro-N-(2-ethyl-6-methylphenyl)-N-(2-methoxy-1-methylethyl)acetamide; 2-chloro-2',6'-diethyl-N-(2-propyloxyethyl)acetanilide; N-(3,4-dichlorophenyl)-propionamide; N-(3,4-dichlorophenyl)methacrylamide; N-(3-chloro-4-methylphenyl)-2-methylpentanamide; N-(3,4-dichlorophenyl)trimethylacetamide; N-(3,4-dichlorophenyl)-alpha,alpha-dimethylvaleramide; N-isopropyl-N-phenylchloroacetamide; N-n-butoxymethyl-N-(2,6-diethylphenyl)chloroacetamide; N-methoxymethyl-N-(2,6-diethylphenyl)chloroacetamide;

OXYPHENOXY HERBICIDES 2-(4-(2,4-Dichlorophenoxy)phenoxy)methyl propionate; methyl 2-(4-(3-chloro-5-(trifluoromethyl)-2-pyridinyloxy)-phenoxy)propanoate; butyl (R)-2-[4-[5-(trifluoromethyl)-2-pyridinyloxy]-phenoxy]propionate; ethyl 2-[4-[(6-chloro-2-benzoxazolyl)oxy]phenoxy]-propanoate; butyl 2-[4-[[5-(trifluoromethyl)-2-pyridinyl]oxy]phenoxy]propionate; 2-[4-[(6-chloro-2-quinoxalinyl)oxy]phenoxy]propionic acid, ethyl ester;

URACILS

5-Bromo-3-s-butyl-6-methyluracil; 5-bromo-3-cyclohexyl-1,6-dimethyluracil; 3-cyclohexyl-5,6-trimethyleneuracil; 5-bromo-3-isopropyl-6-methyluracil; 3-tert-butyl-5-chloro-6-methyluracil;

NITRILES 2,6-Dichlorobenzonitrile; diphenylacetonitrile; 3,5-dibromo-4-hydroxybenzonitrile; 3,5-diiodo-4-hydroxybenzonitrile;

OTHER ORGANIC HERBICIDES

2-Chloro-N,N-diallylacetamide; N-(1,1-dimethyl-2-propynyl)-3,5-dichlorobenzamide; maleic hydrazide; 3-amino-1,2,4-triazole; monosodium methanearsonate; disodium methanearsonate; N,N-dimethyl-alpha,alpha-diphenylacetamide; N-N-di(n-propyl)-2,6-dinitro-4-(trifluoromethyl)aniline; N,N-di(n-propyl)-2,6-dinitro-4-methylaniline; N,N-di(n-propyl)-2,6-dinitro-4-methylsulfonylaniline; O-(2,4-dichlorophenyl)-O-methyl isopropylphosphoramidothioate; 4-amino-3,5,6-trichloropicolinic acid; 2,3-dichloro-1,4-naphthoquinone; di(methoxythiocarbonyl)disulfide; 3-(1-methylethyl)-1H-2,1,3-benzothiadiazin-(4)3H-one-2,2-dioxide; 6,7-dihydrodipyridol[1,2-a:2',1'-c]pyrazidiium salts; 1,1'-dimethyl-4,4'-bipyridinium salts; 3,4,5,6-tetrahydro-3,5-dimethyl-2-thio-2H-1,3,5-thiadiazine; 2-[1-(ethoxyimino)butyl]-5-[s-(ethylthio)propyl]-3-hydroxy-2-cyclohexen-1-one; 2-(2-chlorophenyl)methyl-4,4-dimethyl-3-isoxazolidinone; N-(1-ethylpropyl)-3,4-dimethyl-2,6-dinitrobenzamide; 4-chloro-5-(methylamino)-2-(α,α,α-trifluoro-m-toluyl)-3-(2H)-pyridazinone; 2-(3,5-dichlorophenyl)-2-(2,2,2-trichloromethyl)oxirane;

When mixtures of herbicides are employed, the relative proportions which are used will depend upon the crop to be treated and the degree of selectivity in weed control desired. The herbicidal activity of the 6-arylpyrimidines of the present invention towards a number of common weeds was evaluated using a greenhouse method of testing. Using the procedures described below, the aryl pyrimidines of the present invention were evaluated for control of weeds selected from the following:

| Monocots | |
|---|---|
| Barnyardgrass (BYG) | *Echinochloa crus-galli* |
| Foxtail (FOX) | *Setaria viridis* |
| Johnsongrass (JON) | *Sorghum halepense* |
| Nutsedge (NUT) | *Cyperus esculentus* |
| Wild Oat (WO) | *Avena fatua* |

| Dicots | |
|---|---|
| Cocklebur (CKL) | *Xanthium strumarium* |
| Morningglory (MG) | *Ipomoea lacunosa* |
| Pigweed (PIG) | *Amaranthus retroflexus* |
| Smartweed (SMT) | *Polygonum lapathifolium* |
| Velvetleaf (VEL) | *Abutilon theophrasti* |

The following test procedure was employed. Seeds of selected plants were planted in flats or pots. For preemergence tests, immediately after planting, the test compound was sprayed directly onto the soil surface. The flats or pots were placed in the greenhouse and then watered. For postemergence tests, the seeds were allowed to germinate and grow for 10 to 21 days. Before application, each series of test plants was selected for uniformity, size and stage of development. The test plants were then treated with the test compound, returned to the greenhouse and watered.

The compound to be evaluated was dissolved in an appropriate solvent, usually acetone, and sprayed over the flats or pots using a carrier volume equivalent to 25 or 50 gallons per acre at the rate of application in pounds per acre (lb./A) specified in the table. About two or three weeks after application of the test compound, the state of growth of the plant was observed. Each species was evaluated on a scale of 0–100 in which 0 equals no activity and 100 equals total control. The following Table 3 show the results obtained for the test compounds at the application rate of four pounds per acre and are provided merely as illustrations and are not to be considered as limitations or restrictions of the scope of this invention which is defined by the claims.

TABLE 3

| Cmpd. No. | TYPE TEST | CKL | MG | PIG | SMT | VEL | BYG | FOX | JON | NUT | WO |
|---|---|---|---|---|---|---|---|---|---|---|---|
| 1 | PRE | 10 | 90 | 100 | 100 | 95 | 100 | 100 | 100 | 10 | 100 |
| 1 | POST | 0 | 0 | 0 | 0 | 0 | 0 | 0 | 0 | 0 | 0 |
| 2 | PRE | 0 | 100 | 100 | 100 | 90 | 100 | 100 | 60 | 10 | 90 |
| 2 | POST | 0 | 10 | 15 | 0 | 0 | 20 | 15 | 0 | 0 | 0 |
| 3 | PRE | 0 | 80 | 90 | 100 | 60 | 100 | 100 | 100 | 10 | 95 |
| 3 | POST | 0 | 25 | 15 | 15 | 0 | 30 | 50 | 10 | 0 | 0 |
| 4 | PRE | 0 | 25 | 100 | 65 | 0 | 80 | 95 | 0 | 0 | 20 |
| 4 | POST | 0 | 0 | 0 | 0 | 0 | 0 | 0 | 0 | 0 | 0 |
| 5 | PRE | 0 | 100 | 90 | 80 | 50 | 100 | 100 | 90 | 10 | 95 |
| 5 | POST | 0 | 10 | 15 | 0 | 0 | 20 | 15 | 0 | 0 | 0 |
| 6 | PRE | 0 | 30 | — | — | 0 | 100 | 100 | 60 | 0 | 55 |
| 6 | POST | 0 | 0 | 0 | 0 | 0 | 0 | 0 | 0 | 0 | 0 |
| 7 | PRE | 0 | 0 | — | 0 | 0 | 10 | 0 | 0 | 0 | 0 |
| 7 | POST | 0 | 0 | 0 | 0 | 0 | 0 | 0 | 0 | 0 | 0 |

It is to be understood that changes and variations may be made without departing from the spirit and scope of the invention as defined by the appended claims.

What is claimed is:

1. A compound of the formula

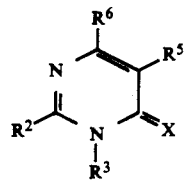

wherein
(a) $R^2$ is a hydrogen, straight $(C_1-C_6)$alkyl, branched $(C_3-C_8)$alkyl, $(C_2-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, $(C_1-C_4)$alkoxy$(C_1-C_4)$alkyl, $(C_1-C_6)$alkylthio, $(C_1-C_6)$alkoxy, $(C_1-C_3)$alkoxycarbonyl, $(C_1-C_3)$alkoxycarbonyl$(C_1-C_3)$alkyl, ar$(C_1-C_4)$alkyl, cyclo$(C_3-C_7)$alkyl, $(C_1-C_3)$alkylamino, di$(C_1-C_3)$alkylamino, di$(C_1-C_3)$alkylaminocaryl, halo or cyano group; and
(b) $R^3$ is a $(C_1-C_4)$alkyl, $(C_3-C_6)$alkenyl, $(C_3-C_6)$alkynyl, halo- or polyhalo$(C_1-C_6)$alkyl group; and
(c) $R^5$ is a $(C_1-C_4)$alkyl; $(C_2-C_6)$alkenyl; or $(C_2-C_6)$alkynyl group; or $(C_5-C_6)$alkenylnyl group, or $(C_1-C_4)$alkoxy$(C_1-C_4)$alkyl group; provided that when $R^6$ is phenyl or substituted phenyl, then $R^5$ is not $(C_1-C_4)$alkyl; and
(d) $R^6$ is a furyl, phenyl, pyridyl, or thienyl group, each of said group is optionally substituted with up to three substituents independently selected from bromo; chloro; fluoro; $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl; polyhalo$(C_2-C_6)$alkynyl; $(C_1-C_{12})$alkylthio, $(C_1-C_{12})$alkylsulfonyl; $(C_1-C_{12})$alkylsulfinyl; phenyl; phen$(C_1-C_{12})$alkyl; phen$(C_2-C_{12})$alkenyl; phen$(C_2-C_{12})$alkynyl; cyano; halo$(C_1-C_6)$alkoxy, carbo$(C_1-C_6)$alkoxy, and nitro group; and
(e) X is oxygen or sulfur.

2. The compound of claim 1 wherein $R^2$ is a methyl, ethyl, n-propyl, n-butyl, n-hexyl, i-propyl, i-butyl or t-butyl group; or methoxy or ethoxy group; or ethoxycarbonyl group; or but-2-ynyl, but-3-ynyl, or prop-2-ynyl group; or fluoro, bromo, or chloro group; or trifluoromethyl or pentafluoroethyl group; or methylthio group; or methoxymethyl group; or benzyl group; or cyclopropyl or cyclobutyl group; or dimethylamino group; or dimethylaminocarbonyl group; or allyl group.

3. The compound of claim 1 wherein $R^3$ is a methyl or ethyl group; or prop-2-ynyl group; or allyl group; or trifluoromethyl group.

4. The compound of claim 1 wherein $R^5$ is a methyl or ethyl group; or allyl group; or prop-2-ynyl or but-2-ynyl group; or methoxymethyl group; or pent-4-en-2-yn-1-yl group.

5. The compound of claim 1 wherein $R^6$ is a phenyl, 2-fluorophenyl, 3-fluorophenyl, 4-fluorophenyl, 3-chlorophenyl, or 3,5-difluorophenyl group.

6. The compound of claim 1 wherein X is oxygen.

7. The compound of claim 1 selected from 2,3-dimethyl-6-phenyl-5-propargyl-4(3H)-pyrimidinone; 3-methyl-6-phenyl-5-propargyl-2-propyl-4(3H)-pyrimidinone; 2,3-diethyl-6-phenyl-5-propargyl-4(3H)-pyrimidinone; 3-ethyl-6-phenyl-5-propargyl-2-trifluoromethyl-4(3H)-pyrimidinone; and 3-ethyl-2-isopropyl-6-phenyl-5-propargyl-4(3H)-pyrimidinone.

8. A method of controlling a weed comprising applying to said weed or to the locus of said weed or to the growth medium of said weed a herbicidally effective amount of a compound of the formula:

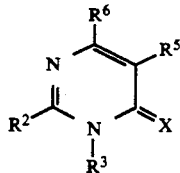

wherein
(a) $R^2$ is a hydrogen, straight $(C_1-C_6)$alkyl, branched $(C_3-C_8)$alkyl, $(C_2-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, $(C_1-C_4)$alkoxy$(C_1-C_4)$alkyl, $(C_1-C_6)$alkylthio, $(C_1-C_6)$alkoxy, $(C_1-C_3)$alkoxycarbonyl, $(C_1-C_3)$alkoxycarbonyl$(C_1-C_3)$alkyl, ar$(C_1-C_4)$alkyl, cyclo$(C_3-C_7)$alkyl, $(C_1-C_3)$alkylamino, di$(C_1-C_3)$alkylamino, di$(C_1-C_3)$alkylaminocarbonyl, halo or cyano group; and
(b) $R^3$ is a $(C_1-C_4)$alkyl, $(C_3-C_6)$alkenyl, $(C_3-C_6)$alkynyl, halo- or polyhalo$(C_1-C_6)$alkyl group; and
(c) $R^5$ is a $(C_1-C_4)$alkyl; $(C_2-C_6)$alkenyl; or $(C_2-C_6)$alkynyl group; or $(C_5-C_6)$alkenynyl group, or $(C_1-C_4)$alkoxy$(C_1-C_4)$alkyl group; and
(d) $R^6$ is a furyl, phenyl, pyridyl, or thienyl group, each of said group is optionally substituted with up to three substituents independently selected from bromo; chloro; fluoro; $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl; polyhalo$(C_2-C_6)$alkynyl; $(C_1-C_{12})$alkoxy, $(C_1-C_{12})$alkylthio, $(C_1-C_{12})$alkylsulfonyl; $(C_1-C_{12})$alkylsulfinyl; phenyl; phen$(C_1-C_{12})$alkyl; phen$(C_2-C_{12})$alkenyl; phen$(C_2-C_{12})$alkynyl; cyano; halo$(C_1-C_6)$alkoxy; carbo$(C_1-C_6)$alkoxy; and nitro group; and
(e) X is oxygen or sulfur.

9. A composition comprising a carrier and a herbicidally effect amount of a compound of the formula:

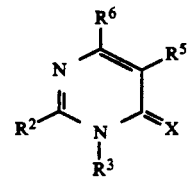

wherein
(a) $R^2$ is a hydrogen, straight $(C_1-C_6)$alkyl, branched $(C_3-C_8)$alkyl, $(C_2-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, $(C_1-C_4)$alkoxy$(C_1-C_4)$alkyl, $(C_1-C_6)$alkylthio, $(C_1-C_6)$alkoxy, $(C_1-C_3)$alkoxycarbonyl, $(C_1-C_3)$alkoxycarbonyl$(C_1-C_3)$alkyl, ar$(C_1-C_4)$alkyl, cyclo$(C_3-C_7)$alkyl, $(C_1-C_3)$alkylamino, di$(C_1-C_3)$alkylamino, di$(C_1-C_3)$alkylaminocarbonyl, halo or cyano group; and
(b) $R^3$ is a $(C_1-C_4)$alkyl, $(C_3-C_6)$alkenyl, $(C_3-C_6)$alkynyl, halo- or polyhalo$(C_1-C_6)$alkyl group; and
(c) $R^5$ is a $(C_1-C_4)$alkyl; $(C_2-C_6)$alkenyl; or $(C_2-C_6)$alkynyl group; or $(C_5-C_6)$alkenynyl group, or $(C_1-C_4)$alkoxy$(C_1-C_4)$alkyl group; and
(d) $R^6$ is a furyl, phenyl, pyridyl, or thienyl group, each of said group is optionally substituted with up to three substituents independently selected from bromo; chloro; fluoro; $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl; polyhalo$(C_2-C_6)$alkynyl; $(C_1-C_{12})$alkoxy, $(C_1-C_{12})$alkylthio, $(C_1-C_{12})$alkylsulfonyl; $(C_1-C_{12})$alkylsulfinyl; phenyl; phen$(C_1-C_{12})$alkyl; phen$(C_2-C_{12})$alkenyl; phen$(C_2-C_{12})$alkynyl; cyano; halo$(C_1-C_6)$alkoxy; carbo$(C_1-C_6)$alkoxy; and nitro group; and
(e) X is oxygen or sulfur.

* * * * *